(12) United States Patent
Carnes et al.

(10) Patent No.: US 6,827,766 B2
(45) Date of Patent: Dec. 7, 2004

(54) DECONTAMINATING SYSTEMS CONTAINING REACTIVE NANOPARTICLES AND BIOCIDES

(75) Inventors: Corrie L. Carnes, Topeka, KS (US); Kenneth J. Klabunde, Manhattan, KS (US); Olga Koper, Manhattan, KS (US); Lisa S. Martin, Fort Riley, KS (US); Kyle Knappenberger, Manhattan, KS (US); Paul S. Malchesky, Painesville Township, OH (US); Bill R. Sanford, Naples, FL (US)

(73) Assignee: United States Air Force, Wright-Patterson Air Force Base, OH (US)

( * ) Notice: Subject to any disclaimer, the term of this patent is extended or adjusted under 35 U.S.C. 154(b) by 150 days.

(21) Appl. No.: 10/267,986

(22) Filed: Oct. 8, 2002

(65) Prior Publication Data

US 2004/0067159 A1 Apr. 8, 2004

(51) Int. Cl.$^7$ .............................. A62D 3/00; A61L 2/16
(52) U.S. Cl. ................ 106/15.05; 106/18.3; 106/18.32; 106/18.33; 106/18.34; 106/18.35; 106/18.36; 422/28; 424/405; 424/489; 424/600; 424/617; 424/641; 424/650; 424/688; 424/689; 424/690; 424/691; 424/692; 424/693; 424/722; 588/200; 588/205; 588/224; 588/231; 588/236; 588/238; 588/242; 588/246
(58) Field of Search ............................ 106/15.05, 18.3, 106/18.32, 18.33, 18.34, 18.35, 18.36; 422/28; 424/405, 489, 600, 617, 641, 650, 688, 689, 690, 691, 692, 693, 722; 588/200, 205, 224, 231, 236, 238, 242, 246

(56) References Cited

U.S. PATENT DOCUMENTS

| 5,990,373 | A | * | 11/1999 | Klabunde | 588/200 |
| 6,057,488 | A | * | 5/2000 | Koper et al. | 588/200 |
| 6,403,653 | B1 | * | 6/2002 | Hobson et al. | 514/759 |
| 6,410,603 | B1 | * | 6/2002 | Hobson et al. | 514/759 |
| 6,413,446 | B1 | * | 7/2002 | Mechtel et al. | 252/181 |
| 6,417,423 | B1 | * | 7/2002 | Koper et al. | 588/200 |
| 6,653,519 | B2 | * | 11/2003 | Koper et al. | 588/200 |
| 6,660,713 | B2 | * | 12/2003 | Carter et al. | 510/507 |
| 2002/0035032 | A1 | * | 3/2002 | Koper et al. | 502/201 |

FOREIGN PATENT DOCUMENTS

WO    WO03059070 A1 * 7/2003

\* cited by examiner

Primary Examiner—Anthony J. Green (57) ABSTRACT

Improved area decontamination products and methods of use thereof are provided which include reactive nanoparticles (e.g., metal oxides, hydroxides and mixtures thereof) with one or more biocides and a liquid carrier for the nanoparticles and biocide(s). The products may be formulated for area decontamination as sprays, fogs, aerosols, pastes, gels, wipes or foams, and the presence of reactive nanoparticles enhances the neutralization of undesirable chemical or biological compounds or agents. The nanoparticles may be from the group consisting of the alkali metal, alkaline earth metal, transition metal, actinide and lanthanide oxides and hydroxides and mixtures thereof. In preferred forms, nanocrystalline oxides and hydroxides of Al, Ca, Ce, Mg, Sr, Sn, Ti and Zn are employed having single crystallite sizes of up to about 20 nm and surface areas of at least about 15 m$^2$/g.

55 Claims, 3 Drawing Sheets

DECONTAMINATING SYSTEMS CONTAINING REACTIVE NANOPARTICLES AND BIOCIDES

BACKGROUND OF THE INVENTION

1. Field of the Invention

The present invention is broadly concerned with decontamination products useful for the neutralization of chemical and biological compounds or agents, such as chemical weapon (CW) and biological weapon (BW) agents and environmental contaminants such as toxic industrial chemicals (TIC's) and toxic industrial materials (TIM's) and biologicals such as spores, bacteria, fungi, molds and viruses. More particularly, the invention is concerned with such products which may be in liquid form as sprayable or foamable products for example, together with corresponding application methods and devices permitting area decontamination. The decontamination products advantageously include a quantity of nanoscale metal particles (e.g., nanoparticulate metal oxides, hydroxides and mixtures thereof), a biocide and a liquid carrier for the nanoparticles and biocide.

2. Description of the Prior Art

Governments around the world have become increasingly concerned about the effects of chemical and/or biological warfare agents, industrial chemicals and other types of hazardous substances, particularly in light of the recent rise in terrorism. The potentially catastrophic results which could ensue in high density population centers subjected to such agents are well known to disaster experts. In addition concerns over environmental contaminants, chemical and biological, including industrial chemicals, raise concerns over public safety. A number of proposals have been adopted for dealing with CW, BW, industrial chemicals, environmental contaminants and similar substances.

There are currently two general types of decontamination methods for biological agents, namely chemical disinfection and physical decontamination. Chemical disinfectants such as hypochlorite solutions are useful but are corrosive to most metals and fabrics, and to human skin. Liquid-like foam disinfectants have also been used, and generally require water and pressurized gases for efficient application. Physical decontamination usually involves dry heat up to 160° C. for 2 hours or steam or super-heated steam for about 20 minutes. Sometimes UV light can be used effectively, but it is generally difficult to implement in actual practice. Techniques used for decontamination of areas subjected to chemical warfare agents, TICs and TIMs are more varied, and depend principally upon the nature of the agent in question.

U.S. Pat. No. 5,914,436 describes methods for the destruction of unwanted compounds such as chlorocarbons, chlorofluorocarbons and PCBs, making use of metal oxide composites as adsorbents. Also, U.S. Pat. No. 6,057,488 describes the use of metal oxide nanoparticles for the destructive adsorption of biological and chemical contaminants, including biological and chemical warfare agents and environmental contaminants. However, these references do not describe techniques for the rapid use of metal oxides in emergency-type situations.

Sandia National Laboratories has recently developed a foam decontamination product referred to as "Sandia Decon Formulation" and includes solubilizing compounds such as cationic surfactants and hydrotropes together with reactive compound(s) such as nucleophilic and oxidizing compounds. The Sandia foam products are available from EnviroFoam Technologies of Huntsville, Ala., and Modec, Inc. of Denver, Colo., and are described in PCT Publication WO 02/02192 published Jan. 10, 2002 and incorporated by reference herein. However, the Sandia Decon Formulation does not make use of reactive metal oxide or hydroxide nanoparticles.

SUMMARY OF THE INVENTION

The present invention overcomes the problems outlined above and provides improved decontamination products adapted for rapid, large-scale area decontamination by neutralization of a variety of undesirable toxants, i.e., any chemical or biological compound, constituent, species or agent that through its chemical or biological action can cause death, temporary or permanent incapacitation or harm to humans or animals. Neutralization refers to the mitigation, detoxification, decontamination or other destruction of toxants to the extent that they no longer cause significant adverse effects.

Broadly speaking, the decontamination products of the invention include a quantity of nanoparticles selected from the group consisting of metal oxides, metal hydroxides and mixtures thereof, one or more biocides and a liquid carrier for the nanoparticles and biocide. The preferred products are formulated for application as liquids, sprays, fogs, aerosols, pastes, gels and foams, depending upon the desired mode of application and end use.

The nanoparticles are preferably selected from the group consisting of the alkali metal, alkaline earth metal, transition metal, actinide and lanthanide oxides and hydroxides, and mixtures thereof, more preferably, the nanoparticles are selected from the group consisting of Al, Ca, Ce, Mg, Sn, Sr. Ti and Zn and mixtures thereof. Particularly preferred nanoparticles, from the standpoints of cost and ease of preparation as well as effectiveness, are selected from the group consisting of Al, Ca, Mg, Ti and Zn. The nanoparticles most useful in the invention comprise single crystallites or polycrystallite aggregations having an average crystallite size of up to about 20 nm, and more preferably from about 2–10 nm. Such crystallites or polycrystallate aggregates also advantageously have a BET surface area of at least about 15 $m^2/g$., and more preferably from about 20–1200 $m^2/g$, most preferably from about 90–600 $m^2/g$.

A virtually unlimited number of biocides in addition to the nanoparticles can be used in the context of the invention, for example biocides selected from the group individually or mixtures thereof consisting of biocidally active peroxides including hydrogen peroxide, mono- and polyfunctional alcohols, aldehydes, acids, ozone, naphtha compounds and compounds containing an alkali metal, a transition metal, a Group III or Group IV metal, a sulfur, a nitrogen, or a halogen atom. Particular biocides are those selected from the group consisting of formaldehyde, glutaraldehyde, peracetic acid, the alkali metal hypochlorites, quaternary ammonium compounds, 2-amino-2-methyl-1-propanol, cetyltrimethylammonium bromide, cetylpyridinium chloride, 2,4,4-trichloro-2-hydroxydiphenylether, 1-(4-chlorophenyl)-3-(3, 4-dichlorophenyl) urea, zinc oxide, zinc ricinoleate, pentachlorophenol, copper naphthenate, tributyltin oxide, dichlorophen, p-nitrophenol, p-chloro-m-xylenol, beta-naphthol, 2,3,5,6-tetrachloro-4-(methyl sulfonyl)-pyridine, salicylanilide, bromoacetic acid, alkyl quaternary ammonium acetate, sodium ethyl mercuric thiosalicylate, sodium orthophenyl phenate, n-alkyl ($C_{12}$ to $C_{18}$) dimethyl benzyl ammonium chloride, the organoborates, 2,2-(1- methyltrimethylenedioxy)-bis-(4-methyl-1,3,2-dioxaborinane), 2,2-oxybis(4,4,6-trimethyl)-1,3,2-dioxaborinane, ethylene glycol monomethyl ether, parahydroxy benzoates, organic boron compounds, 8-hydroxyquinoline, sodium pentachlorophenate, dimethyl-ethylalkylbenzyl ammonium chloride, alkylammonium salts of 2-pyridinethiol-1-oxide, 1,3,5-triethylhexahydro-1,3,5-triazine, strontium chromate, the halogenated phenols, 2-bromo-4-phenylphenol, the silver salts such as silver nitrate, silver chloride, silver oxide and elemental silver, the organic peroxides, silver sulfadiazine, sodium dichloro-s-triazinetrione, dyhydrate-4-chloro-2-cyclo-hexylphenol, 2-chloro-4-nitrophenol, the substituted paraffins, 3-chloro-3-nitro-2-butanol, 2-chloro-2-nitro-1-butanol stearate, 2-chloro-2-nitrobutyl acetate, 4-chloro-4-nitro-3-hexanol, 1-chloro-1-nitro-1-propanol, 2-chloro-2-nitro-1-propanol, triethyltin chloride, 2,4,5-trichlorophenol, 2,4,6-trichlorophenol, 2,2-thiobis(3,4,6-trichlorophenol), 1,3-dichloro-5,5-dimethylhydantoin, tris(hydoxy-methyl) nitromethane, the nitroparaffins. 2-nitro-2-ethyl-1,3-propanediol dipropionate, 2-nitro-2-ethyl-1,3-propanediol, 2-nitro-2-methyl-1,3-propanediol, hexahydro-1,3,5-tris(2-hydroxy-ethyl)-s-triazine, 1,3,5-tris(tetrahydro-2-furanyl)-methyl-hexahydro-s-triazine, methyl bisthiocyanate, 2,2-dibromo-3-nitrilopropionamide, β-bromo-β-nitrostyrene, fluorinated compounds, N-ethyl-N-methyl-4-(trifluoromethyl)-2-(3,4-dimethoxyphenyl) benzamide, pentachlorophenol, dichlorophene, orthophenyl phenol, di-bicyclo-(3,1,1 or 2,2,1)-heptyl and di-bicyclo-(3,1,1 or 2,2,1)-heptenyl polyamines.

The liquid carriers for the nanoparticles and biocide are generally selected from the group consisting of solvents (both aqueous and non-aqueous), dispersants and emulsion systems and combinations thereof. The solvents are generally capable of solvating the biocide fraction of the products, but in many instances are incapable of solvating the nanoparticles, which may also incorporate the antimicrobial agent on the nanoparticle. As the name implies, the dispersants are used to create dispersions or suspensions which are not true solutions. The emulsion systems may be oil-in-water or water-in-oil systems and generally are made up of respective quantities of oil, water and surfactant. The surfactants may be of nonionic, cationic or anionic nature, and the oils may be natural or synthetic.

Generally speaking, the nanoparticle fraction of the products should be present at a level of from about 0.1 to 40% by weight, and more preferably from about 1 to 10% by weight; the biocide fraction should be at a level of from about 0.001 to 10% by weight, and more preferably from about 0.01 to 5% by weight; and the liquid carrier fraction should be present at a level of from about 50 to 99.9% by weight, and more preferably from about 85 to 99% by weight.

In many instances, preparation of the products of the invention involves direct addition of the selected nanoparticles into the liquid carrier, often with supplemental mixing to insure homogeneity. Again depending upon the selected carrier it may be necessary to heat the system to facilitate incorporation of the nanoparticles and/or biocide(s). In the case of emulsions the chosen surfactant(s) may be mixed with the oil fraction and nanoparticles, followed by heating and addition of water, or can be mixed with the water. The formulation is preferably a single solution, but the individual components of the solution may be packaged separately.

The preferred products of the invention, depending upon the type and quantity of reactive nanoparticles and biocide (s) selected, have an extremely broad effectiveness against toxants. Such would include CW agents, BW agents, TICs and TIMs (e.g., sarin, soman, VX, mustard, spore forming bacterium such as anthrax, vegetative bacterium such as plague and cholera, virus such as smallpox, yellow fever, fungi and molds, and bacterial toxins such as botulism, ricin and those from fungi and molds). Additionally, chemical toxants include but are not limited to o-alkyl phosphonofluoridates, such as sarin and soman, o-alkyl phosphoramidocyanidates, such as tabun, o-alkyl, s-2-dialkyl aminoethyl alkylphosphonothiolates and corresponding alkylated or protonated salts, such as VX, mustard compounds, including 2-chloroethylchloromethylsulfide, bis(2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl)ether, and bis(2-chloroethylthioethyl)ether, Lewisites, including 2-chlorovinyldichloroarsine, bis(2-chlorovinyl) chloroarsine, tris(2-chlorovinyl)arsine, bis(2-chloroethyl) ethylamine, and bis(2-chloroethyl)methylamine, saxitoxin, ricin, alkyl phosphonyldifluoride, alkyl phosphonites, chlorosarin, chlorosoman, amiton, 1,1,3,3,3,-pentafluoro-2-(trifluoromethyl)-1-propene, 3-quinuclidinyl benzilate, methylphosphonyl dichloride, dimethyl methylphosphonate, dialkyl phosphoramidic dihalides, alkyl phosphoramidates, arsenic trichloride, diphenyl hydroxyacetic acid, quinuclidin-3-ol, dialkyl aminoethyl-2-chlorides, dialkyl aminoethane-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphorous oxychloride, alkyl phosphites, phosphorous trichloride, phosphorus pentachloride, alkyl phosphites, sulfur monochloride, sulfur dichloride, thionyl chloride, acetaldehyde, acetone, acrolein, acrylamide, acrylic acid, acrylonitrile, aldrin/dieldrin, aluminum, americium, ammonia, aniline, antimony, arsenic, asbestos, atrazine, barium, benzene, benzidine, 2,3-benzofuran, beryllium, 1,1'-biphenyl, bis(2-chloroethyl) ether, bis(chloromethyl)ether, boron, bromodichloromethane, bromoform, bromomethane, 1,3-butadiene, 1-butanol, 2-butanone, 2-butoxyethanol, butraldehyde, cadmium, carbon disulfide, carbon tetrachloride, carbonyl sulfide, cesium, chlordane, chlordecone and mirex, chlorfenvinphos, chlorinated dibenzo-p-dioxins (CDDs), chlorine, chlorobenzene, chlorodibenzofurans (CDFs), chloroethane, chloroform, chloromethane, chlorophenols, chlorpyrifos, chromium, cobalt, copper, crankcase oil, creosote, cresols, cyanide, cyclohexane, DDT, DDE, DDD, DEHP, di(2-ethylhexyl)phthalate, diazinon, dibromochloropropane, 1,2-dibromoethane, 1,4-dichlorobenzene, 3,3'-dichlorobenzidine, 1,1-dichloroethane, 1,2-dichloroethane, 1,1-dichloroethene, 1,2-dichloroethene, 1,2-dichloropropane, 1,3-dichloropropene, dichlorvos, diethyl phthalate, diisopropyl methylphosphonate, di-n-butylphtalate, 1,3-dinitrobenzene, dinitrocresols, dinitrophenols, 2,4- and 2,6-dinitrotoluene, 1,2-diphenylhydrazine, di-n-octylphthalate (DNOP), 1,4-dioxane, dioxins, disulfoton, endosulfan, endrin, ethion, ethylbenzene, ethylene oxide, ethylene glycol, fluorides, formaldehyde, freon 113, fuel oils, gasoline, heptachlor and heptachlor epoxide, hexachlorobenzene, hexachlorobutadiene, hexachlorocyclohexane, hexachlorocyclopentadiene, hexachloroethane, hexamethylene diisocyanate, hexane, 2-hexanone, HMX (octogen), hydraulic fluids, hydrazines, hydrogen sulfide, iodine, isophorone, jet fuels, kerosene, lead, malathion, manganese, MBOCA, mercury, methanol, methoxychlor, 2-methoxyethanol, methyl ethyl ketone, methyl isobutyl ketone, methyl mercaptan, methyl parathion, methyl t-butyl ether, methylchloroform, methylene chloride, methylenedianiline, methyl methacrylate, methyl-tert-butyl ether, mirex and chlordecone, mustard gas, N-nitrosodimethylamine, N-nitrosodiphenylamine, N-nitrosodi-n-propylamine, naphthalene, nickel, nitrobenzene, nitrophenols, otto fuel, perchloroethylene, pentachlorophenol, phenol, phosphorus, plutonium, polybrominated biphenyls (PBBs), polychlorinated biphenyls (PCBs), polycyclic aromatic hydrocarbons (PAHs), propylene glycol, phthalic anhydride, pyrethrins and pyrethroids, pyridine, radium, radon, RDX (cyclonite), selenium, silver, strontium, styrene, sulfur dioxide, sulfur trioxide, sulfuric acid, 1,1,2,2-tetrachloroethane, tetrachloroethylene, tetryl, thallium, thorium, tin, titanium tetrachloride, toluene, total petroleum hydrocarbons (TPH), toxaphene, trichlorobenzene, 1,1,1-trichloroethane, 1,1,2-trichloroethane, trichloroethylene (TCE), 1,2,3-trichloropropane, 1,2,4-trimethylbenzene, 1,3,5-trinitrobenzene, 2,4,6-trinitrotoluene (TNT), uranium, vanadium, vinyl acetate, vinyl chloride, xylene and zinc.

The products of the invention can be applied in a variety of ways. Thus, the products may be formulated for specific end use applications such as by spraying, aerosolization, wiping, fogging or as a foam. In any event, an area to be decontaminated is treated by applying the product to or in the vicinity of the area using the product, generally at a temperature in the range of from about −50 to 300° C., most usually at or about ambient temperature. If desired, a decontamination apparatus may be provided in the form of a container holding a quantity of the product and having an applicator operatively coupled with the container; such applicators may be selected from the group consisting of a spray nozzle, fog nozzle, foam nozzle, a wipe, a paste applicator and a gel applicator. In many instances, the product is pressurized or can be pressurized within the container typically at a level of from about 25–250 psi. A propellant may also be used such as those selected from the group consisting of $N_2$, the noble gases, carbon dioxide, air, volatile hydrocarbons, hydrofluorocarbons, fluorocarbons and mixtures thereof.

DETAILED DESCRIPTION OF THE PREFERRED EMBODIMENTS

EXAMPLES

The following examples set forth preferred products and methods in accordance with the invention. It is to be understood, however, that these examples are provided by way of illustration and nothing therein should be taken as a limitation upon the overall scope of the invention.

Example 1

In this example, commercially available Sandia decontamination foam (Sandia Decon 100 foam, EnviroFoam Technologies) was supplemented with reactive nanoparticles in order to improve the performance of the product. The improved foam was prepared by suspending MgO and CaO with respective quantities of the Sandia foam solution at room temperature using a magnetic stirrer. The solutions were made up of 95% by weight Sandia foam and either nanoparticulate MgO or nanoparticulate CaO at 5% by weight.

Paraoxon Study

Figure 1:
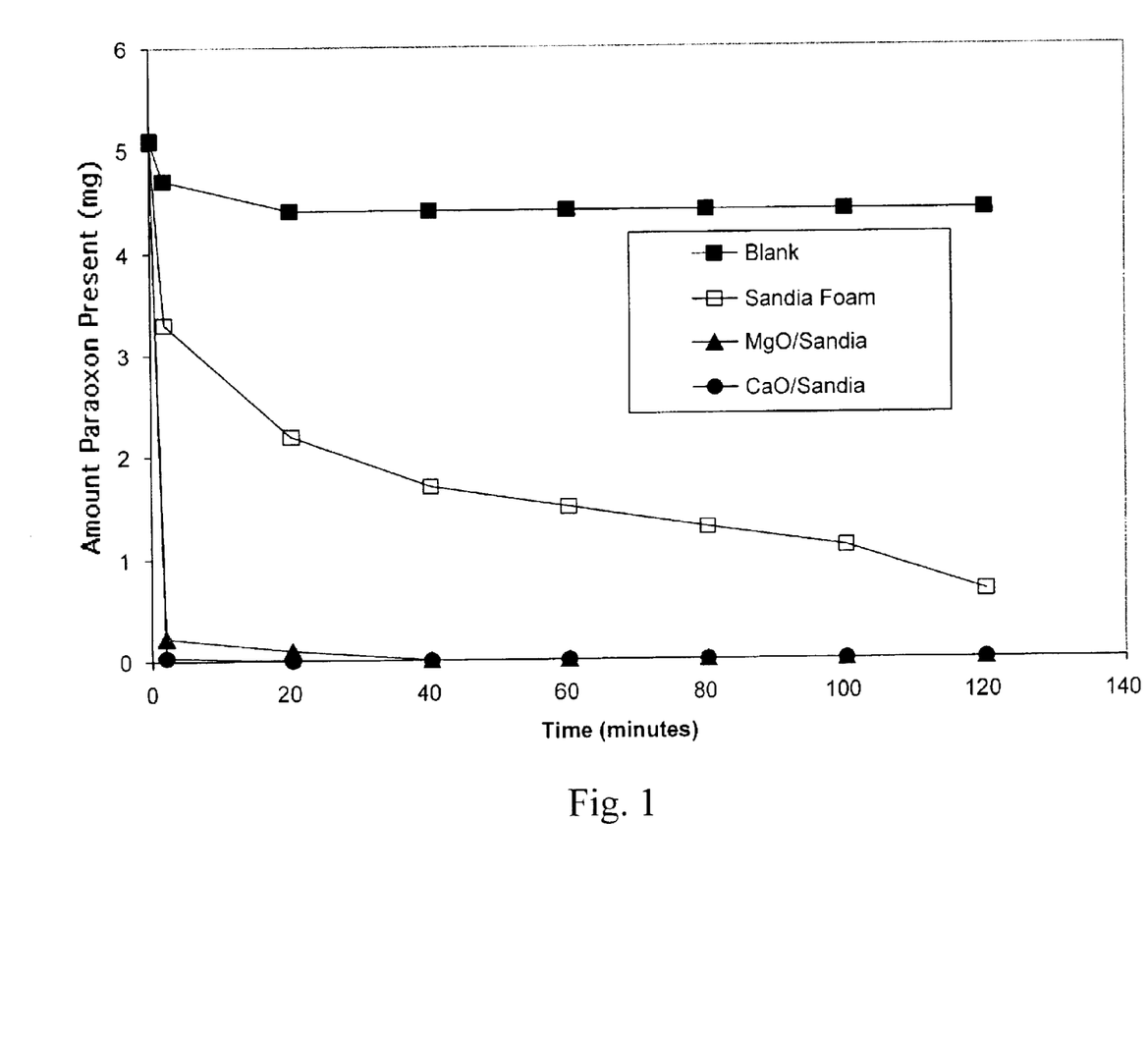
FIG. 1 is a graph illustrating the ambient temperature neutralization of paraoxon over time, using commercially available Sandia foam and Sandia foam supplemented with MgO and CaO nanoparticles, as described in Example 1.
Figure 2:
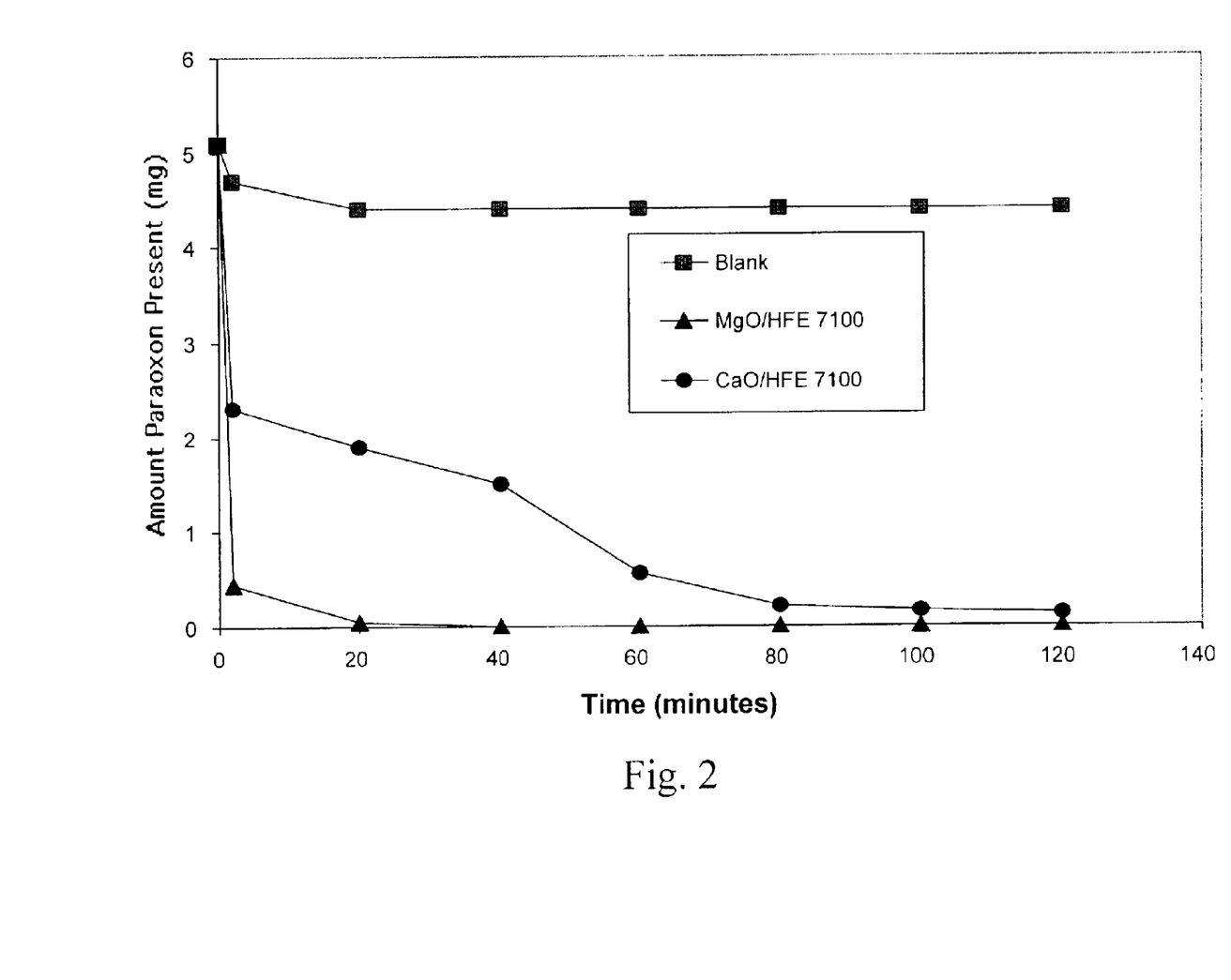
FIG. 2 is a graph illustrating the ambient temperature neutralization of paraoxon over time, using commercially available HFE 7100 solvent supplemented with MgO and CaO nanoparticles, as described in Example 2.
Figure 3:
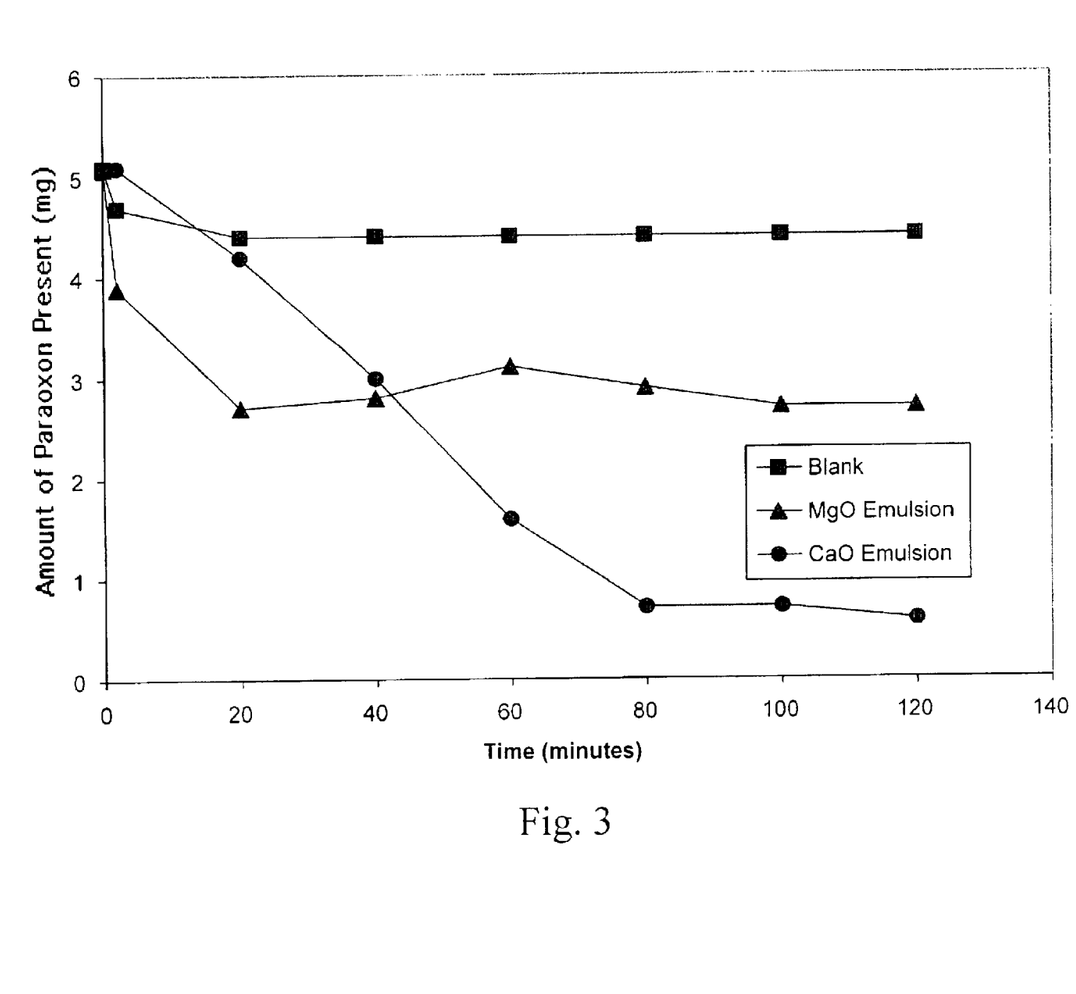
FIG. 3 is a graph illustrating the ambient temperature neutralization of paraoxon over time, using water/oil emulsions supplemented with MgO and CaO nanoparticles, as described in Example 3.

A paraoxon test was used to study the chemical reactivities of the nanoparticulate MgO/Sandia and CaO/Sandia foam solution products, versus the original Sandia foam solution. The disappearance of paraoxon, a simulant for nerve agents, was monitored using UV-Vis spectroscopy using paraoxon's very distinctive feature around 268 nm. In these tests, 200 ml of pentane was placed in a round bottom flask and 4 µl of paraoxon was added and allowed to dissolve. Next, 4 g of the respective test solution was added to the flask and the scans were taken for 120 minutes in two and twenty minute increments. The equivalent amount of the Sandia foam solution was also studied as a comparison. FIG. 1 illustrates the amount of paraoxon present versus time for the samples. The absorbance of the paraoxon band went to zero in all of the Sandia/nanoparticle products, indicating complete adsorption. Sandia foam solution alone was not nearly as effective and the kinetics of the paraoxon reduction were much slower than that of the combined nanoparticle/Sandia foam solution products.

2-CEES Study

The chemical reactivity of the nanoparticulate MgO and CaO/Sandia foam products versus the original foam was studied by monitoring the adsorption and destructive adsorption of 2-chloroethyl ethyl sulfide (2-CEES, a simulant for mustard gas) via GCMS. During this study, 2-CEES was loaded at 10 wt % (agent/emulsion×100) into 100 mg of the MgO/Sandia foam solution and CaO/Sandia foam solution in 4 dram vial. The mixtures were capped and vortex mixed for 20 seconds. The reaction was carried out at room temperature and atmospheric pressure for 2 hours. After 2 hours, 10 ml of extractive solvent was added to each system (n-hexane for 2-CEES) and the reaction vials were sonicated for 20 minutes followed by 5 minutes of centrifugation to separate phases. A 5 ml aliquot of each formulation was taken and 5 µl of internal standard (n-decane) was added. Each extract was then analyzed by GC/MS.

The solutions that performed the best were those having the lowest amount of recoverable 2-CEES in the extract. The MgO/Sandia foam solution and CaO/Sandia foam solution formulations were tested as follows: a blank consisting of a vial with 2-CEES only, Sandia foam solution only, MgO/Sandia foam solution, and CaO/Sandia foam solution. In the 2-CEES challenge the Sandia foam solution and the 5% nanoparticulate MgO/Sandia foam solution had no extractable 2-CEES.

Biological Membrane Tests with *Bacillus subtilus* Spores

Biological membrane tests with *Bacillus subtilus* spores were conducted to determine the biological activity of the MgO/Sandia foam solution. Nitrocellulose membranes for each trial and the control were placed in 60×13 mm sterile petri dishes and inoculated with 200 µL of *B. subtilus* spores solution (1.5×10⁻⁴), and were allowed to dry for 1 hour. After drying, respective membranes were inoculated with 5 ml of the MgO/Sandia foam solution and an equivalent amount of Sandia foam solution products were in distilled water, and were allowed to soak. Samples were taken at time intervals of 30 and 60 minutes. After the desired contact time was reached, the foam products were removed and the membranes were rinsed in 10 ml of sterile phosphate buffer solution to elute the spores. After the expiration of 10 minutes, 200 $\mu$L of the PBS solution was plated on nutrient agar (in triplicate) and incubated for 24 hours at 37° C. Colonies were counted and compared to the controls to determine percent kill and log kill. The results showed that there was 100% kill found at both 30 and 60 minutes with the Sandia foam solution and the MgO/Sandia foam solution producing an estimated reduction of 4 log kill (see Table 1). The combined nanoparticle/Sandia foam solution performed as well as the Sandia foam solution alone, demonstrating that the presence of the nanoparticles did not inhibit the efficiency of the foam solution for biological kill.

TABLE 1

| Formulation | 30 Minute Percent Kill | 30 Minute Estimated Log Kill | 60 Minute Percent Kill | 60 Minute Estimated Log Kill |
|---|---|---|---|---|
| Sandia Foam | 100 | 4 | 100 | 4 |
| MgO/Sandia Foam | 100 | 4 | 100 | 4 |

Example 2

In this example, MgO and CaO nanoparticles were suspended in commercially available HFE 7100 solution at a level of 95% by weight HFE 7100 and 5% by weight MgO or CaO.

Paraoxon Study

A paraoxon test was used to study the chemical reactivities of the nanoparticulate MgO/HFE and CaO/HFE solutions, versus the original HFE solvent. The disappearance of paraoxon was monitored using UV-Vis spectroscopy at 268 nm, using the same procedure set forth in Example 1. FIG. 2 illustrates the amount of paraoxon present versus time for the blank, MgO/HFE 7100 and CaO/HFE 7100 samples. The MgO/HFE 7100 and CaO/HFE 7100 solutions were found to have very high activity, destroying most of the paraoxon in a short time period (see FIG. 2).

2-CEES and DMMP Studies:

The chemical reactivities of the MgO/HFE 7100 and CaO/HFE 7100 solutions and the original HFE 7100 solvent were studied by monitoring the adsorption and destructive adsorption of 2-chloroethyl ethyl sulfide (2-CEES) and dimethylmethyl phosphonate (DMMP) challenge agents via GCMS, using the procedure described in Example 1.

In the 2-CEES challenge, the MgO/HFE 7100 had the highest percent reduction at 40% followed by the nanoparticulate CaO/HFE 7100 which reduced 32% of the 2-CEES. Additionally, the nanoparticle formulations showed the presence of ethyl vinyl sulfide, demonstrating the destructive adsorptive nature of the combined nanoparticle formulations. The HFE 7100 solvent and blank samples reduced 12% and 14% respectively of the 2-CEES, as shown in Table 2. In the DMMP challenge, the CaO/HFE 7100 had the highest percent reduction at 45% followed by the MgO/HFE 7100 which reduced 33% of the DMMP. The HFE 7100 solvent and blank samples reduced 15% and 13% respectively of the DMMP (Table 2).

TABLE 2

| Sample | Percent Reduction of Challenge Agent 2-CEES | DMMP |
|---|---|---|
| 5% CaO/HFE 7100 | 32 | 45 |
| 5% MgO/HFE 7100 | 40 | 33 |
| HFE 7100 solvent | 12 | 15 |
| Blank | 14 | 13 |

Biological Membrane Tests with *E. herbicola*

Nitrocellulose membranes for each trial were inoculated with 200 μl *E. herbicola* overnight, followed by allowing the membranes to dry for approximately 1 hour. After drying, each membrane was inoculated with 5 ml of the MgO/HFE 7100 or CaO/HFE 7100 nanoparticle solution. Samples were taken at various time intervals. After the desired contact time was reached, the membranes were rinsed in 10 ml of PBS and eluted for 10 minutes. 200 μl of each final solution was then plated onto a nutrient agar plate and incubated for 24 hours at 37° C. Colonies were counted and compared to the controls to determine percent kill. As seen in Table 3, the nanoparticle-containing solutions had very high biocidal activity toward the *E. herbicola*. Both of the solutions were 100% effective after 45 minutes. However, the CaO/HFE 7100 nanoparticle solution produced 100% kill at the 15 minute time interval.

TABLE 3

| Time | MgO in HFE-7100 | | CaO in HFE-7100 | |
|---|---|---|---|---|
| (minutes) | % Kill | Log Kill | % Kill | Log Kill |
| 15 | 50 | 0.30 | 100 | 4 |
| 30 | 69.5 | 0.52 | 100 | 4 |
| 45 | 100 | 4 | 100 | 4 |
| 60 | 100 | 4 | 100 | 4 |

Other HFE solvents can also be used in lieu of or in combination with the HFE-7100, such as HFE-71DA, HFE-711PA and HFE-7500 and others.

Example 3

In this example, nanoparticle-containing emulsions in accordance with the invention were formulated and tested. These emulsions were prepared by first mixing the surfactant (Triton-X114 [nonionic octylphenol ethylene oxide condensate] for CaO and $Ca(OH)_2$ and AOT [anionic, dioctyl sulfosuccinate, sodium salt] for MgO and ZnO), oil (vegetable) and the selected nanoparticles (MgO, CaO or ZnO) at room temperature. The mixtures were then heated at 85° C. for one hour with stirring. Water was then injected into each formulation completing the emulsions. Each emulsion unless otherwise indicated was a 5/1 water/oil emulsion and contained 2% by weight nanoparticles.

Paraoxon Study

A paraoxon test was used to study the chemical reactivities of the MgO and CaO emulsion formulations versus control emulsions without nanoparticles. The test procedure used is described in Example 1. FIG. 3 illustrates the amount of paraoxon present versus time for the samples. It was found that the MgO and CaO emulsions destroyed a much larger percent of the paraoxon than did the blank emulsion without nanoparticles. This study was repeated with nanoparticulate MgO two weeks after the emulsion was prepared, and the same results were found.

Biological Membrane Tests with *Bacillus subtilus* Spores Biological membrane tests with *B. subtilus* spores were conducted to determine the biological activity of the nanoparticulate CaO and ZnO emulsions, using the procedure described in Example 1. As seen in Table 4, the CaO emulsion (7:1), Ca(OH)$_2$ emulsion and ZnO emulsion produced very high kills between 98.9–100%, after 24 hours of contact.

TABLE 4

| Components of Emulsions/Solutions: | Decontamination of *B. subtilus* spores after 24 hours of contact | |
|---|---|---|
| | % Kill | Log Kill |
| CaO/Triton-X/oil (7:1) | 100 | 4 |
| Ca(OH)$_2$/AOT/water/oil | 99.9 | 3 |
| ZnO/AOT/water/oil | 98.9 | 2 |

What is claimed is:

1. A decontamination product comprising:
   a quantity of nanoparticles selected from the group consisting of metal oxides, metal hydroxides, and mixtures thereof;
   from about 0.001 to 10% by weight of a biocide; and
   a liquid carrier for said nanoparticles and biocide.

2. The product of claim 1, said nanoparticles selected from the group consisting of the alkali metal, alkaline earth metal, transition metal, actinide and lanthanide oxides and hydroxides, and mixtures thereof.

3. The product of claim 2, said nanoparticles selected from the group consisting of Al, Ca, Ce, Mg, Sr, Sn, Ti, and Zn oxides and hydroxides and mixtures thereof.

4. The product of claim 3, said nanoparticles selected from the group consisting of Mg, Ca, Al, Ti, and Zn oxides and hydroxides and mixtures thereof.

5. The product of claim 1, said nanoparticles comprising single crystallites or polycrystallite aggregations having an average crystallite size of up to about 20 nm.

6. The product of claim 5, said average crystallite size being from about 2–10 nm.

7. The product of claim 1, said nanoparticles comprising single crystallite or polycrystallite aggregations having a BET surface area of at least about 15 m$^2$/g.

8. The product of claim 7, said surface area being from about 20–1200 m$^2$/g.

9. The product of claim 8, said surface area being from about 90–600 m$^2$/g.

10. The product of claim 1, said biocide being selected from the group consisting of biocidally active peroxides, mono- and polyflinctional alcohols, aldehydes, acids, ozone, naphtha compounds and compounds containing an alkali metal, a transition metal, a Group III or Group IV metal, a sulfur, a nitrogen, or a halogen atom.

11. The product of claim 10, said biocide selected from the group consisting of formaldehyde, glutaraldehyde, peracetic acid, hydrogen peroxide, alcohols, the alkali metal hyperchlorites, quaternary ammonium compounds, 2-amino-2-methyl-1-propanol, cetyltrimethylammonium bromide, cetylpyridinium chloride, 2,4,4-trichloro-2-hydroxydiphenylether, 1-(4-chlorophenyl)-3-(3,4-dichlorophenyl) urea, zinc oxide, zinc ricinoleate, pentachlorophenol, copper naphthenate, tributyltin oxide, dichlorophene, p-nitrophenol, p-chloro-m-xylenol, beta-naphthol, 2,3,5,6-tetrachloro-4-(methyl sulfonyl)-pyridine, salicylanilide, bromoacetic acid, alkyl quaternary ammonium acetate, sodium ethyl mercuric thiosalicylate, sodium orthophenyl phenate, n-alkyl (C$_{12}$ to C$_{18}$) dimethyl benzyl ammonium chloride, the organoborates, 2,2-(1-methyltrimethylenedioxy)-bis-(4-methyl-1,3,2-dioxaborinane), 2,2-oxybis(4,4,6-trimethyl)-1,3,2-dioxaborinane, ethylene glycol monomethyl ether, parahydroxy benzoates, organic boron compounds, 8-hydroxyquinoline, sodium pentachlorophenate, dimethylethylalkylbenzyl ammonium chloride, alkylammonium salts of 2-pyridinethiol-1-oxide, 1,3,5-triethylhexahydro-1,3,5-triazine, strontium chromate, the halogenated phenols, 2-bromo-4-phenylphenol, the silver salts including silver nitrate, silver chloride, silver oxide, elemental silver, the organic peroxides, silver sulfadiazine, sodium dichloro-s-triazinetrione, dyhydrate-4-chloro-2-cyclo-hexylphenyl, 2-chloro-4-nitrophenol, the substituted paraffins, 3-chloro-3-nitro-2-butanol, 2-chloro-2-nitro-1-butanol stearate, 2-chloro-2-nitrobutyl acetate, 4-chloro-4-nitro-3-hexanol, 1-chloro-1-nitro-1-propanol, 2-chloro-2-nitro-1-propanol, triethyltin chloride, 2,4,5-trichlorophenol, 2,4,6-trichlorophenol, 2,2-thiobis(3,4,6-trichlorophenol), 1,3-dichloro-5,5-dimethylhydantoin, tris(hydoxy-methyl) nitromethane, the nitroparaffins. 2-nitro-2-ethyl-1,3-propanediol 20,2-nitro-2-ethyl-1,3-propanediol, 2-nitro-2-methyl-1,3-propanediol, hexahydro-1,3,5-tris(2-hydroxyethyl)-s-triazine, 1,3,5-tris(tetrahydro-2-furanyl)-methyl-hexahydro-s-triazine, methyl bisthiocyanate, 2,2-dibromo-3-nitrilopropionamide, β-bromo-β-nitrostyrene, fluorinated compounds, N-ethyl-N-methyl-4-(trifluoromethyl)-2-(3,4-dimethoxyphenyl) benzamide, pentachlorophenol, dichlorophene, orthophenyl phenol, di-bicyclo-(3,1,1 or 2,2, 1)-heptyl and di-bicyclo-(3,1,1 or 2,2,1)-heptenyl polyamines and mixtures thereof.

12. The product of claim 1, said carrier selected from the group consisting of solvents, dispersants and emulsion systems.

13. The product of claim 12, said solvents selected from the group consisting of aqueous and non-aqueous solvents.

14. The product of claim 12, said emulsion systems including respective quantities of oil, water and surfactant.

15. The product of claim 1, said nanoparticles being present at a level of from about 0.1–40% by weight.

16. The product of claim 15, said nanoparticles being present at a level of from about 1–10% by weight.

17. The product of claim 1, said biocide being present at a level of from about 0.01–5% by weight.

18. The product of claim 1, said carrier being present at a level of from about 50–99.9% by weight.

19. The product of claim 18, said carrier being present at a level of from about 85–99% by weight.

20. The product of claim 1, said product being formulated for application as a liquid, spray, fog, aerosol, paste, gel, wipe, vapor or foam.

21. The product of claim 20, said product being formulated for application as a spray or foam.

22. A method of decontaminating an area comprising the step of applying to said area a product in accordance with claim 1.

23. The method of claim 22, said applying step being carried out at a temperature of from about −50 to 300° C.

24. The method of claim 23, said applying step comprising the step of applying said product as a liquid, spray, fog, aerosol, paste, gel, wipe, vapor or foam.

25. The method of claim 24, said applying step comprising the step of applying said product as a liquid or foam.

26. A decontamination apparatus comprising a container holding a quantity of a product in accordance with claim 1, with an applicator operatively coupled with said container for selective application of said product from the container.

27. The apparatus of claim 26, said applicator selected from the group consisting of a spray nozzle, fog nozzle, foam nozzle, a paste applicator, a gel applicator, vapor nozzle and a wipe applicator.

28. The apparatus of claim 26, said product being pressurized within said container or in containers that can be pressurized.

29. The apparatus of claim 28, said pressure being at a level of from about 0–250 psi within said container.

30. The apparatus of claim 29, including a propellant within said container.

31. The apparatus of claim 30, said propellant selected from the group consisting of $N_2$, the noble gases, carbon dioxide, air, volatile hydrocarbons, fluorocarbons, hydrofluorocarbons and mixtures thereof.

32. A decontamination product comprising:
a quantity of nanoparticles selected from the group consisting of metal oxides, metal hydroxides, and mixtures thereof, said nanoparticles comprising single crystallite or polycrystallite aggregations having a BET surface area of at least about 15 $m^2/g$;
a biocide; and
a liquid carrier for said nanoparticles and biocide.

33. The product of claim 32, said surface area being from about 20–1200 $m^2/g$.

34. The product of claim 33, said surface area being from about 90–600 $m^2/g$.

35. A decontamination product comprising:
a quantity of nanoparticles selected from the group consisting of metal oxides, metal hydroxides, and mixtures thereof;
a biocide; and
a liquid carrier for said nanoparticles and biocide, said carrier selected from the group consisting of solvents, dispersants and emulsion systems, said emulsion systems including respective quantities of oil, water and surfactant.

36. A decontamination product comprising:
a quantity of nanoparticles selected from the group consisting of metal oxides, metal hydroxides, and mixtures thereof;
a biocide; and
from about 85–99% by weight of a liquid carrier for said nanoparticles and biocide.

37. A decontamination product comprising:
a quantity of nanoparticles selected from the group consisting of metal oxides, metal hydroxides, and mixtures thereof, said nanoparticles comprising single crystallite or polycrystallite aggregations having a BET surface area of at least about 15 $m^2/g$; and
a biocide.

38. The product of claim 37, said biocide being intermingled with said nanoparticles.

39. The product of claim 37, said nanoparticles selected from the group consisting of the alkali metal, alkaline earth metal, transition metal, actinide and lanthanide oxides and hydroxides, and mixtures thereof.

40. The product of claim 37, said biocide being selected from the group consisting of biocidally active peroxides, mono- and polyfunctional alcohols, aldehydes, acids, ozone, naphtha compounds and compounds containing an alkali metal, a transition metal, a Group III or Group IV metal, a sulfur, a nitrogen, or a halogen atom.

41. The product of claim 37, said biocide being present at a level of from about 0.001–10% by weight.

42. A method of decontaminating an area comprising the step of applying to said area a product in accordance with claim 37.

43. The method of claim 42, said applying step comprising the step of applying said product as a liquid, spray, fog, aerosol, paste, gel, wipe, vapor or foam.

44. A decontamination product comprising:
a quantity of nanoparticles selected from the group consisting of metal oxides, metal hydroxides, and mixtures thereof dispersed in a liquid carrier; and
a biocide,
said nanoparticles comprising single crystallite or polycrystallite aggregations having a BET surface area of at least about 15 $m^2/g$.

45. The product of claim 44, said biocide being intermingled with said nanoparticles.

46. The product of claim 44, said nanoparticles selected from the group consisting of the alkali metal, alkaline earth metal, transition metal, actinide and lanthanide oxides and hydroxides, and mixtures thereof.

47. The product of claim 44, said biocide being selected from the group consisting of biocidally active peroxides, mono- and polyfunctional alcohols, aldehydes, acids, ozone, naphtha compounds and compounds containing an alkali metal, a transition metal, a Group III or Group IV metal, a sulfur, a nitrogen, or a halogen atom.

48. The product of claim 44, said biocide being present at a level of from about 0.001–10% by weight.

49. A method of decontaminating an area comprising the step of applying to said area a product in accordance with claim 44.

50. The method of claim 49, said applying step comprising the step of applying said product as a liquid, spray, fog, aerosol, paste, gel, wipe, vapor or foam.

51. A decontamination product comprising:
a quantity of nanoparticles selected from the group consisting of metal oxides, metal hydroxides, and mixtures thereof, said nanoparticles comprising single crystallite or polycrystallite aggregations having a BET surface area of at least about 15 $m^2/g$; and
a vapor biocide.

52. The product of claim 51, said biocide being selected from the group consisting of biocidally active peroxides, mono- and polyfunctional alcohols, aldehydes, acids, ozone, naphtha compounds and compounds containing an alkali metal, a transition metal, a Group III or Group IV metal, a sulfur, a nitrogen, or a halogen atom.

53. The product of claim 51, said nanoparticles selected from the group consisting of the alkali metal, alkaline earth metal, transition metal, actinide and lanthanide oxides and hydroxides, and mixtures thereof.

54. A method of decontaminating an area comprising the step of applying to said area a product in accordance with claim 51.

55. The method of claim 54, said applying step comprising the step of applying said product as a liquid, spray, fog, aerosol, paste, gel, wipe, vapor or foam.

* * * * *

UNITED STATES PATENT AND TRADEMARK OFFICE
CERTIFICATE OF CORRECTION

PATENT NO. : 6,827,766 B2 Page 1 of 1
DATED : December 7, 2004
INVENTOR(S) : Carnes, Corrie L. et al.

It is certified that error appears in the above-identified patent and that said Letters Patent is hereby corrected as shown below:

Title page,
Item [73], Assignee, replace information with the following:
-- NanoScale Materials, Inc.
  Manhattan, Kansas (US) --

Signed and Sealed this

Twenty-second Day of February, 2005

JON W. DUDAS
*Director of the United States Patent and Trademark Office*